(12) United States Patent
Blackadar et al.

(10) Patent No.: US 11,122,994 B2
(45) Date of Patent: Sep. 21, 2021

(54) SYSTEMS AND METHODS FOR INJURY PREVENTION AND REHABILITATION

(71) Applicant: MedStar Health, Washington, DC (US)

(72) Inventors: Thomas Blackadar, Pembroke, MA (US); Carter Mitchell, Bethesda, MD (US)

(73) Assignee: MEDSTAR HEALTH, Washington, DC (US)

( * ) Notice: Subject to any disclaimer, the term of this patent is extended or adjusted under 35 U.S.C. 154(b) by 463 days.

(21) Appl. No.: 16/009,927

(22) Filed: Jun. 15, 2018

(65) Prior Publication Data

US 2018/0360350 A1   Dec. 20, 2018

Related U.S. Application Data

(60) Provisional application No. 62/520,916, filed on Jun. 16, 2017.

(51) Int. Cl.
*A61B 5/11* (2006.01)
*A61B 5/00* (2006.01)
(Continued)

(52) U.S. Cl.
CPC .......... *A61B 5/1121* (2013.01); *A61B 5/1114* (2013.01); *A61B 5/4528* (2013.01);
(Continued)

(58) Field of Classification Search
CPC ..... A61B 5/486; A61B 5/0024; A61B 5/1036; A61B 5/1071; A61B 5/4585;
(Continued)

(56) References Cited

U.S. PATENT DOCUMENTS

2010/0286950 A1* 11/2010 Heijkants ............. A61B 5/6828
702/151
2012/0190505 A1* 7/2012 Shavit ................ A63B 71/0622
482/8
(Continued)

FOREIGN PATENT DOCUMENTS

EP          2057944 A1    5/2009
WO     2017/088047 A1    6/2017

OTHER PUBLICATIONS

Dai, Boyi, et al. "Concurrent tactile feedback provided by a simple device increased knee flexion and decreased impact ground reaction forces during landing." Journal of applied biomechanics 32.3 (2016): 248-253.

(Continued)

*Primary Examiner* — Patrick Fernandes
(74) *Attorney, Agent, or Firm* — Tarolli, Sundheim, Covell & Tummino LLP

(57) ABSTRACT

One aspect of the present disclosure relates to a physical training system for injury prevention and rehabilitation. The training system can include a wearable device in communication with an external device, which can be used to train at least the athlete wearing the wearable device. The wearable device can reduce the number of sensors needed to capture motion data required for the training. For example, the wearable device can include an inertial measurement unit (IMU) device located at a position relative to a joint of an athlete to measure an inertial displacement of the joint and an optical sensor to measure an angle of the joint. The wearable device can include a wireless transceiver to communicate a characteristic of motion of the joint (determined based on data from the IMU and the optical sensor) to an external device.

13 Claims, 13 Drawing Sheets

(51) Int. Cl.
  *G16H 20/30* (2018.01)
  *A61B 5/107* (2006.01)
(52) U.S. Cl.
  CPC .......... *A61B 5/4585* (2013.01); *A61B 5/6812* (2013.01); *A61B 5/6828* (2013.01); *G16H 20/30* (2018.01); *A61B 5/1071* (2013.01); *A61B 2562/0219* (2013.01)
(58) Field of Classification Search
  CPC ... A61B 5/6802; A61B 5/6828; A61B 5/7282; A61B 5/7405; A61B 5/742; A61B 5/7455; A61B 2503/10; A61B 2505/09; A61B 2562/0247; A61B 2562/0261; G09B 19/0038; G06F 19/3481; H04Q 9/00
  See application file for complete search history.

(56) References Cited

U.S. PATENT DOCUMENTS

| | | | |
|---|---|---|---|
| 2012/0253234 A1 | 10/2012 | Yang et al. | |
| 2013/0066448 A1* | 3/2013 | Alonso | H04Q 9/00 700/91 |
| 2013/0244211 A1* | 9/2013 | Dowling | G06F 19/3481 434/247 |
| 2015/0022362 A1* | 1/2015 | Lucas | A61B 5/6828 340/573.7 |
| 2015/0257682 A1* | 9/2015 | Hansen | G16H 20/30 382/103 |
| 2015/0272484 A1* | 10/2015 | Ronchi | A61B 5/1114 600/595 |
| 2017/0042467 A1 | 2/2017 | Herr et al. | |
| 2017/0290683 A1* | 10/2017 | Pelisson | A61F 2/64 |
| 2018/0028109 A1 | 2/2018 | Tesnow | |

OTHER PUBLICATIONS

Tomaru, Akitomo, et al. "A 3-DOF knee joint angle measurement system with inertial and magnetic sensors." Systems Man and Cybernetics (SMC), 2010 IEEE International Conference on. IEEE, 2010.

PCT International Search Report and Written Opinion for corresponding International Application Serial No. PCT/US2018/037793, dated Dec. 11, 2018, pp. 1-23.

* cited by examiner

SYSTEMS AND METHODS FOR INJURY PREVENTION AND REHABILITATION

RELATED APPLICATIONS

This application claims the benefit of U.S. Provisional Application No. 62/520,916, entitled "SYSTEMS AND METHODS FOR INJURY PREVENTION AND REHABILITATION," filed Jun. 16, 2017. The entirety of this application is hereby incorporated by reference for all purposes.

TECHNICAL FIELD

The present disclosure relates generally to physical training and, more specifically, to systems and methods that provide automated physical training.

BACKGROUND

As young athletes play competitive sports, they engage in dynamic motion by running, jumping, landing, moving from side to side, zig-zagging, and otherwise moving dynamically. This participation in competitive sports can increase the risk of injury in these young athletes. Recently, incidents of torn ligaments in the shoulder, elbow, and knee due to non-contact injuries have been rising among these young athletes, particularly young female athletes aged 12-22. Training an athlete's body through exercises helps to strengthen proper muscles, to learn proper joint angle rotation, and to avoid such non-contact ligament tears.

An athlete can be guided through the exercises by a physical trainer, who can observe and correct the athlete's posture and position during each of the exercises. A lone physical trainer is unable to monitor many athletes at a time. Accordingly, during a game situation where many athletes participate at once, if only a single physical trainer is available, many athletes will not be properly observed. The unobserved athletes are at a higher risk of improper joint angle rotation, which puts undue strain on the ligament, leading to a higher risk of ligament injury.

Unfortunately, the number of physical trainers is far less than the number of athletes. Trying to compensate for the lack of physical trainers, systems have been developed that can track body or joint movement. These systems can include a plurality of sensors (e.g., optical sensors or inertial measurement unit (IMU) sensors) that can be placed around the athlete's body to capture motion data. However, the motion data provided through these systems is imprecise, and the systems may impede the athlete's performance.

SUMMARY

The present disclosure relates generally to physical training and, more specifically, to systems and methods for automated physical training. The automated physical training can be used for injury prevention and rehabilitation and/or to increase athlete training compliance.

In one aspect, the present disclosure can include a wearable device for injury prevention and rehabilitation. The wearable device can include an inertial measurement unit (IMU) device located at a position below a knee of an athlete to measure an inertial displacement of a valgus angle of the knee. The wearable device can also include an optical sensor traversing across the knee to measure an angle of the knee and connected to the IMU device. A resistive sensor can serve the same purpose as the optical sensor. A microprocessor can be associated with the IMU device to create a motion data set comprising data related to the inertial displacement of the valgus angle of the knee relative to an anatomical reference frame and data related to the angle of the knee. For example, the motion data set is input to a kinetic algorithm to determine an output indication of motion. The wearable device also includes a power source and a tactile output device coupled to the microprocessor to provide a tactile indication of motion based on the output indication of motion.

In another aspect, the present disclosure can include a physical training system. The system can include an external device that includes a wireless transceiver. The system also includes a plurality of wearable devices. Each wearable device includes an inertial measurement unit (IMU) device located at a position below a joint of a respective athlete to measure an inertial displacement of the joint; an optical sensor traversing across the joint of the respective athlete (or a resistive sensor) to measure an angle of the joint and connected to the IMU device; a microprocessor associated with the IMU device to create a motion data set comprising data related to the inertial displacement of the joint and data related to the angle of the joint, wherein the motion data set is input to a kinetic algorithm to determine an output indication of motion; a wireless transceiver coupled to the microprocessor; an output device coupled to the microprocessor to provide a perceivable indication of a motion of the joint based on the output indication of motion; and a power source. The wireless transceiver of the external device facilitates bidirectional communication with the wireless transceiver of each of the wearable devices.

In a further aspect, the present disclosure can include a personal training method. The method can include calibrating an IMU device of a wearable device worn by an athlete around a joint to set an anatomical reference frame. For each step taken by the athlete, the method can include determining, by the IMU device, a rotation of the joint from the anatomical reference frame, a speed, and a distance traveled, measuring, with an optical sensor or a resistive sensor, an angle of the joint, and determining a characteristic of motion for the joint based on the data recorded by the IMU device and the data recorded by the optical sensor. A wireless transmitter of the wearable device can communicate to an external device the characteristic of motion of the joint associated with the step.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
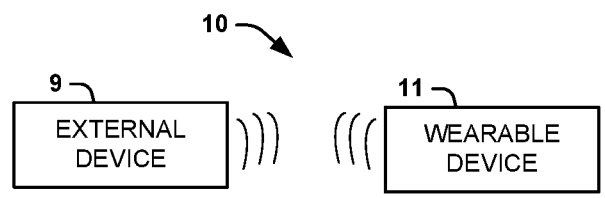
FIG. 1 is a block diagram illustration showing an example of a system, that provides automated physical training to prevent injury and facilitate rehabilitation in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "physical trainer" can refer to an individual who works one-on-one with an athlete to plan or implement an exercise regimen. As used herein, the physical trainer can be a coach, an athletic trainer, a physical therapist, or other individual involved in the monitoring of one or more athletes. In some instances, the physical trainer can be the athlete. The terms "personal trainer" and "physical trainer" can be used interchangeably herein.

As used herein, the term "exercise" can refer to an activity requiring physical effort for the purpose of conditioning any part of the body. In some instances, exercise can be planned, structured, and repetitive.

As used herein, the term "wearable device" can refer to a piece of technology related to health and fitness that can be worn by an athlete. One example of a wearable device can be embodied in a compression garment (a tight, compressive form of clothing that is supportive to a joint).

As used herein, the term "joint" can refer to a part of an athlete's body where two parts of the skeleton are fitted together. For example, a joint can be a knee, a hip, an ankle, a wrist, an elbow, or a shoulder.

As used herein, the term "inertial measurement unit (IMU) device" can refer to a device that measures and reports properties related to an athlete's body, such as a joint. The IMU device can have nine or more degrees of freedom. For example, the IMU device can integrate one or more three-dimensional accelerometers, one or more three-dimensional gyroscopes, and one or more three-dimensional magnetometers, and a microcontroller into a single device. An example of a 9 degree of freedom IMU device is a BNO055 from Bosch Sensortec (Robert Bosch Gmbh, 70839 Gerlingen-Schillerhone, Germany).

As used herein, the term "optical sensor" can refer to a device that detects a variation in a light signal. A fiber optic sensor is an example of an optical sensor.

As used herein, the term "potentiometer" can include any type of instrument used to measure an electric potential or voltage. For example, the potentiometer can be a resistor with a variable resistance value, made of a resistive material through which a current is passed.

As used herein, the term "anatomical reference frame" can refer an abstract coordinate system and a set of anatomical reference points that uniquely fix (locate and orient) the abstract coordinate system and standardize measurements. For example, dour anatomical reference points are sufficient to fully define the three dimensional anatomical reference frame.

As used herein, the term "angle" can refer to a joint angle between two body segments linked by a common joint. One example type of angle is a valgus angle that refers to a joint being turned toward the midline of the body.

As used herein, the term "athlete" can refer to an individual who participates in one or more exercises, sports, or games requiring physical strength, agility, and/or stamina.

As used herein, the term "automate" can refer to converting a process to a largely automatic operation.

As used herein, the term "automatic" can refer to something working by itself with little or no direct human control.

II. Overview

The present disclosure relates generally to physical training of athletes to condition the athlete's body, thereby reducing the risk of non-contact ligament tears. The conditioning generally involves repetitive exercises that train the athlete's joint to perform properly. The athlete benefits most from the exercises with guidance from a physical trainer, ensuring that the athlete performs exercises properly. While athletes benefit from such individualized attention, many athletes cannot receive the individualized attention from a physical trainer because athletes far outnumber physical trainers. To ensure that all athletes receive such individualized attention, the present disclosure is related, more specifically, to systems and methods that provide automated physical training. By automating at least a portion of the physical training process, more athletes can receive the individualized attention that ensures the body is properly conditions to reduce the risk of non-contact injuries. Additionally, the automated process can increase athlete compliance and decrease the cost or expense of training programs or feedback systems for training.

The automated physical training can be provided by a wearable device (e.g., a compression garment) with at least one inertial measurement unit (IMU) and an optical sensor. Notably, the wearable device can reduce the number of sensors needed to capture motion data required for the automated physical training. The wearable device can be worn by an athlete to record a very precise set of motion data required to perform one or more kinetic algorithms to indicate the athlete's movement. In other words, the information provided by the wearable device can be used to train at least the athlete wearing the wearable device (e.g., if a movement is incorrect, a warning can be issued). The wearable device can include a wireless transmitter that can communicate with an external computing device to deliver data from the at least one IMU and the optical sensor. The external computing device can be can be used for individual (self-driven) training of the athlete wearing the external device engaging in predetermined exercises. However, the external computing device can receive data from a plurality of wearable devices to facilitate group training.

III. Systems

As shown in FIG. 1, one aspect of the present disclosure can include a system 10 for automated physical training. The system 10 can train an athlete by teaching the proper way to engage in a dynamic motion, lowering the risk of suffering a non-contact ligament tear in a joint, like the knee, elbow, wrist, shoulder, or the like. Traditionally, such training was done with a human physical trainer in the loop. The system 10 can guide an athlete through predefined exercises in an automated manner so that improper motions are flagged and corrected without requiring a human physical trainer. Indeed, the system 10 can be used for injury prevention and rehabilitation.

The system 10 can include an external device 9 in communication with a wearable device 11. Together, the external device 9 and the wearable device 11 can take the place of a human physical trainer in the loop. The wearable device 11 can sense motion of a joint and send data related to the motion of the joint to the external device 9. The external device 9 can run a program related to specific exercises for the joint and determine whether the motion of the joint is proper. If the motion is improper, the external device 9 and/or the wearable device 11 can provide feedback to the athlete indicating that the motion is improper. For example, the feedback can include an audio, visual, and/or vibrational alarm or indication.

The external device 9 and the wearable device 11 can each include a transmitter to engage in the communication. The communication can be wireless communication according to a long range and/or short range wireless protocol. An example of a transmission according to a long range wireless protocol can include WiFi transmission or cellular transmission. An example of a transmission according to a short range wireless protocol can be a Bluetooth transmission. The transmitters in the external device 9 and the wearable device 11 can be any type of wireless transceiver that is configured to pair or otherwise communicate with each other in a bi-directional manner.

The external device 9 can be a computing device that has at least a non-transitory memory storing instructions and a processor to execute the instructions. Examples of the external device 9 can include a smart watch, a mobile phone, a tablet computing device, a personal computing device (laptop or desktop), or the like. The external device 9 can be associated with the athlete wearing the wearable device for self-guided training. However, the external device 9 can be associated with another person (e.g., a physical trainer) to monitor the athlete and/or a group of athletes (discussed with respect to FIG. 2).

The wearable device 11 can be associated with or worn by the athlete. The wearable device 11 can be associated with a joint of the athlete, such as the knee, ankle, hip, wrist, elbow, spine or shoulder. As an example, the wearable device 11 can be embedded within a compression garment worn over or near the joint. The wearable device 11 can include one or more sensors to record motion data related to motion of the athlete's joint. For example, the one or more sensors can include one or more inertial measurement units (IMUs) and an optical sensor, such as a fiber optic sensor.

The external device 9 can include an application, which is stored in the non-transitory memory and executed by the processor, that executes a physical training routine. The physical training routine can include one or more exercises for a certain joint of a certain difficulty level and a number of repetitions for the one or more exercises. The application can save the information related to the motion data and can determine whether an exercise was performed correctly based on the motion data and further based on one or more scoring metrics for the exercises. The application allows the system 10 to provide objective feedback about motion of an athlete's joint. This can allow the athlete or another individual like a physical trainer to understand how the athlete performs certain exercises or routines. Additionally, the objective feedback provided by the system 10 can improve athlete training compliance and decrease the risk of the athlete suffering a non-contact injury. Moreover, the personal training system can decrease the costs associated with programs to prevent joint injuries.

Figure 2:
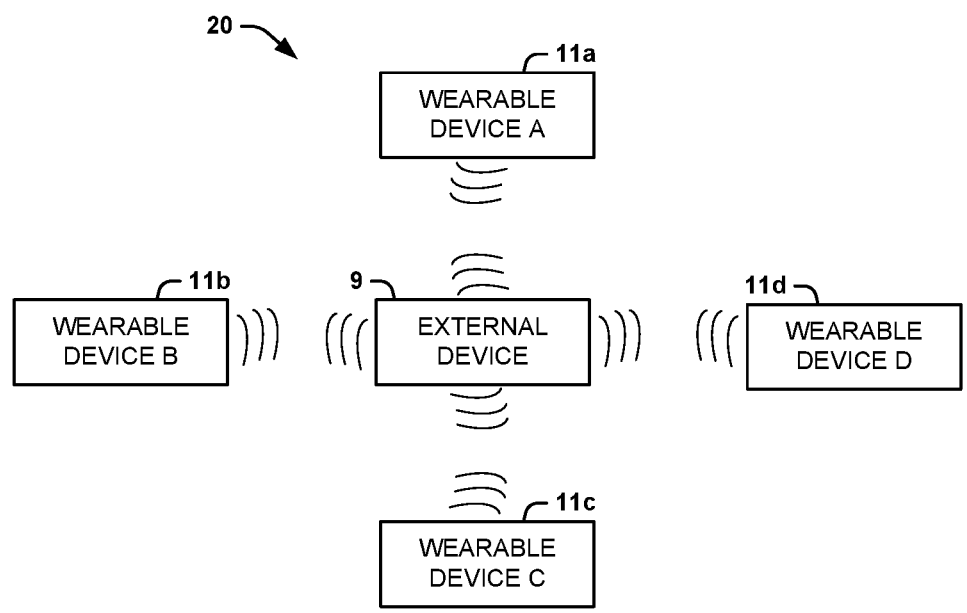
FIG. 2 is a block diagram illustration showing the external device of FIG. 1 interfacing with a plurality of wearable devices.

As shown in FIG. 2, the external device 9 can be associated with a plurality of wearable devices 11a, 11b, 11c, and 11d. In some instances, the plurality of wearable devices 11a, 11b, 11c, and 11d can be associated with a plurality of different athletes (so that a single physical trainer can be responsible for training a plurality of athletes). However, in other instances, the plurality of wearable devices 11a, 11b, 11c, and 11d can be associated with different joints on the same individual.

In any case, the wireless transceiver of the external device 9 facilitates bidirectional communication with the wireless transceivers of the plurality of wearable devices 11a, 11b, 11c, and 11d. The external device 9 and/or each of the plurality of wearable devices 11a, 11b, 11c, and 11d can execute a kinetic algorithm to determine a characteristic of a given motion related to the exercise to allow for monitoring the athlete. Although four wearable devices 11a, 11b, 11c, and 11d are illustrated, it will be understood that any number of wearable devices can be monitored by a given external device.

Figure 3:
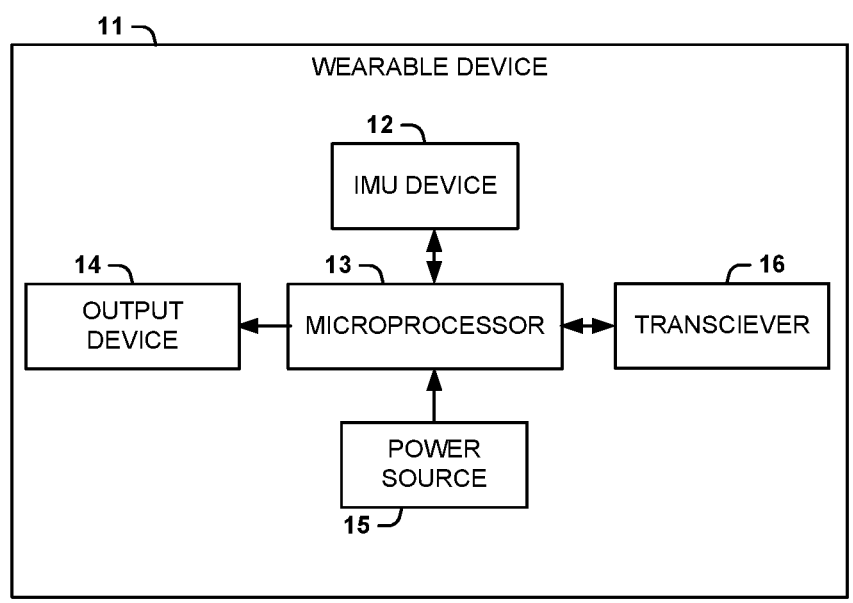
FIG. 3 is a block diagram illustration showing an example configuration of the wearable device of FIG. 1.

An example configuration of the wearable device 11 is shown in FIG. 3. The wearable device 11 can include a single IMU device 12 to measure an inertial displacement of the joint. The IMU device 12 can be a 9 DOF device that can accurately measure the angle of the joint (e.g., the valgus angle with respect to earth). The IMU device 12 can also measure additional information, such as speed, distance traveled, steps taken, stride length, velocity, or the like.

Figure 4:
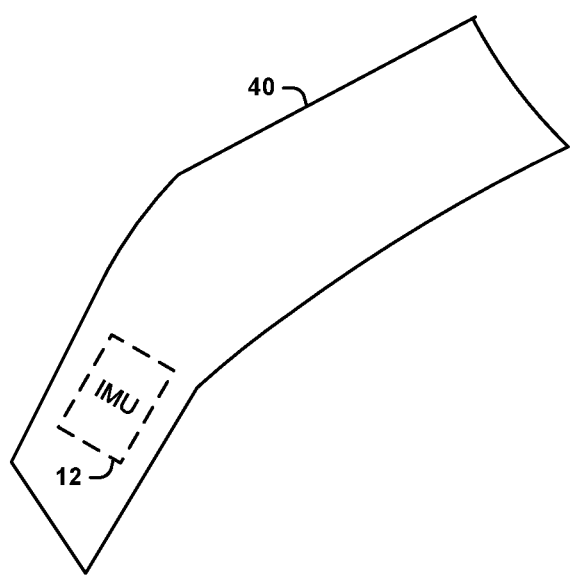
FIG. 4 is a schematic diagram of a compression garment housing the wearable device of FIG. 3.

For example, as shown schematically in FIG. 4, the wearable device 11 can be a compression garment 40 that includes the IMU device 12 therein. The IMU device 12 can be located at a position distal to the joint. For example, when the joint is a knee, the compression garment 40 can be sized and dimensioned to be located around the knee and the IMU can be located at a portion below the knee. In this example, the inertial displacement measured can be the inertial displacement of a valgus angle of the knee. In some instances, the compression garment can include at least a portion having a potentiometric structure.

Referring again to FIG. 3, the wearable device 11 can also include a microprocessor 13 that can be associated with the IMU. The microprocessor 13 can process data related to the inertial displacement determined by the IMU device 12. For example, the microprocessor 13 can process the data relative to a reference frame, such as an anatomical reference frame and/or an earth reference frame. The reference frame can be established using a calibration procedure of the IMU device 12. An initial calibration can occur when the IMU device 12 is stationary. However, a calibration can take place when the IMU device 12 is moving during the exercise. In some instances, the wearable device 11 can communicate with an external device 9 to establish at least a portion of the calibration. The microprocessor 13 can determine whether the motion indicated by the data associated with the inertial displacement is correct/proper or incorrect/improper. In some instances, the external device 9 can communicate with the microprocessor 13 regarding whether the motion indicated by the data associated with the inertial displacement is correct/proper or incorrect/improper based on a characteristic of the motion determined by the microprocessor 13.

The wearable device can also include an output device 14, a power source 15, and the wireless transceiver 16. The output device 14 can be coupled to the microprocessor 13 to provide a perceivable indication of the motion based on the inertial displacement. In some instances, the output device 14 can provide the indication when the motion is deemed to be incorrect. For example, the indication can be a tactile indication, an audio indication, a visual indication, or any combination thereof. The power source 15 can provide power to one or more components of the wearable device 11, such as the IMU device 12, the microprocessor 13, the output device 14, and/or the wireless transceiver 16. For example, the power source 15 can be one or more batteries. It will be understood that the microprocessor 13, the wireless transceiver 16, the power source 15, and/or the output device 14 can be embodied within the compression garment 40 with the IMU device 12.

Figure 5:
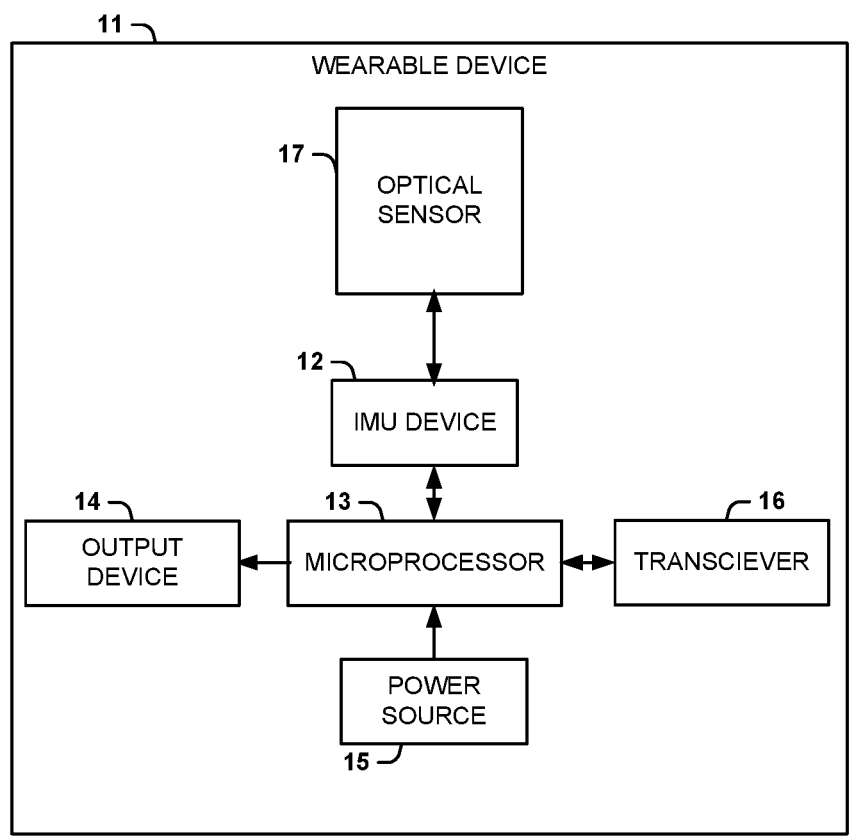
FIG. 5 is another block diagram illustration showing an example configuration of the wearable device of FIG. 1.

Illustrated in FIG. 5, is an example of the wearable device 11 that includes the IMU device 12 and an optical sensor 17 connected to the IMU device. The IMU device 12 and the optical sensor 17 together allow for the reduction in the number of sensors needed to detect motion of the device, providing the ability to capture more motion data and joint angles with a less precise location. For example, the IMU device 12 can measure rotation from a reference frame (as well as other data, such as direction, altitude, life, and the like), while the optical sensor 17 can be used to measure the specific joint angle. The IMU device 12 can include a processor that can take in the data from the optical sensor 17 can determine the joint angle, as well as other functionality.

Figure 6:
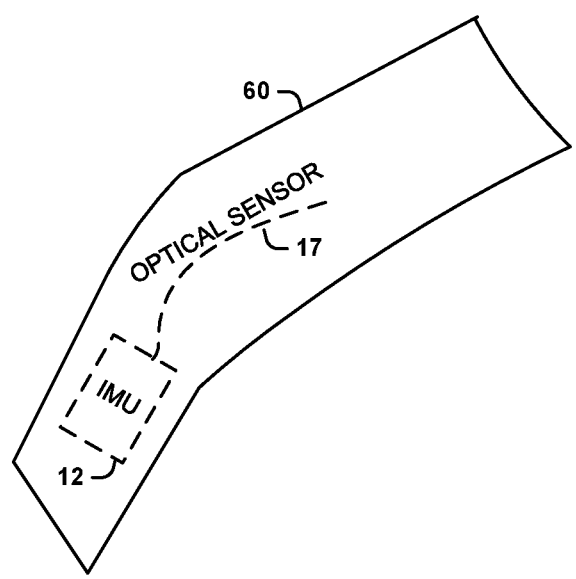
FIG. 6 is a schematic diagram of a compression garment housing the wearable device of FIG. 5.
Figure 7:
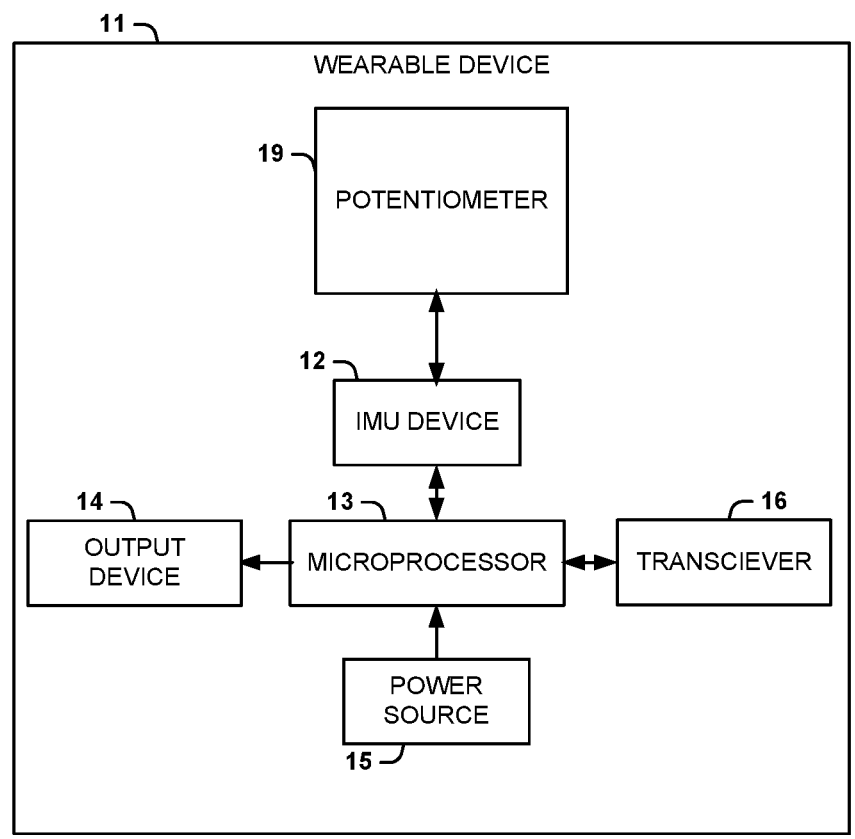
FIG. 7 is another block diagram illustration showing an example configuration of the wearable device of FIG. 1.
Figure 8:
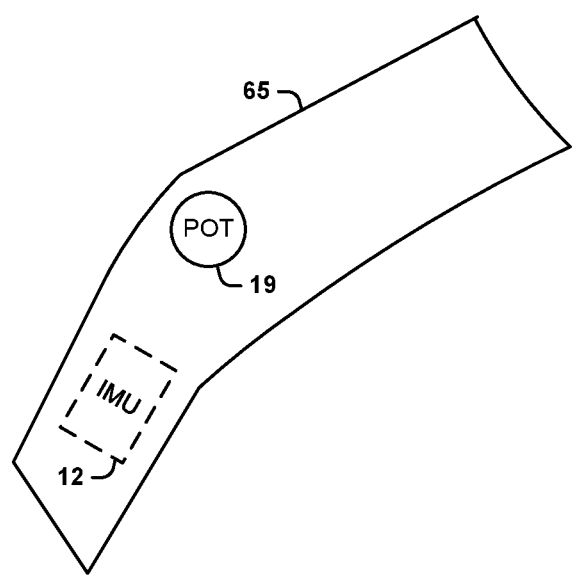
FIG. 8 is a schematic diagram of a compression garment housing the wearable device of FIG. 7.

In some instances, the optical sensor 17 can include a fiber optic sensor. As shown in FIG. 6, the optical sensor 17 can traverse across the joint. Although the optical sensor 17 is shown as traversing the joint in a vertical fashion, it can also alternatively traverse the joint in a horizontal fashion. Within the compression garment 60, the optical sensor 17 can traverse the knee vertically to measure an angle of the knee. In some instances, the optical sensor 17 can traverse the knee vertically on the lateral and/or medial side of the knee. FIGS. 7 and 8 show an example where a potentiometer 19 performs similar functions to the optical sensor 17.

Figure 9:
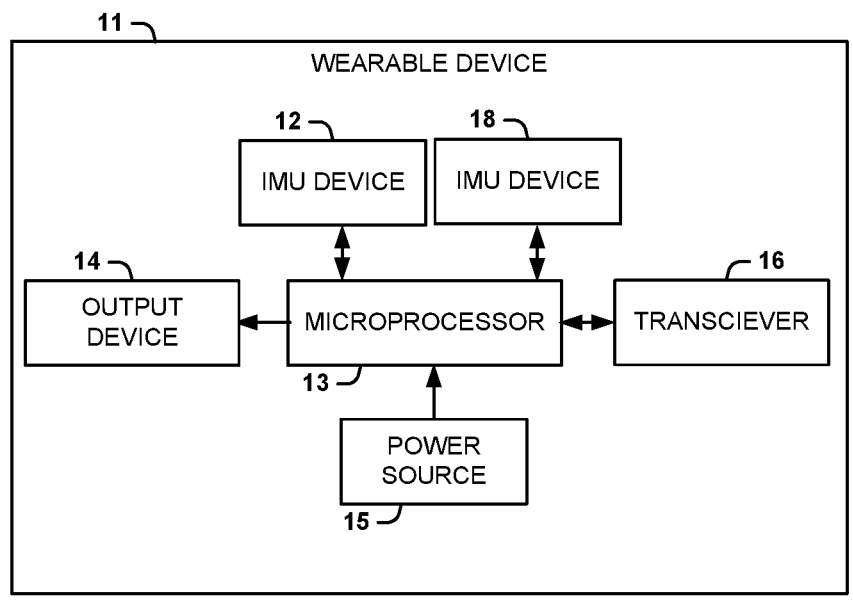
FIG. 9 is another block diagram illustration showing an example configuration of the wearable device of FIG. 1.
Figure 10:
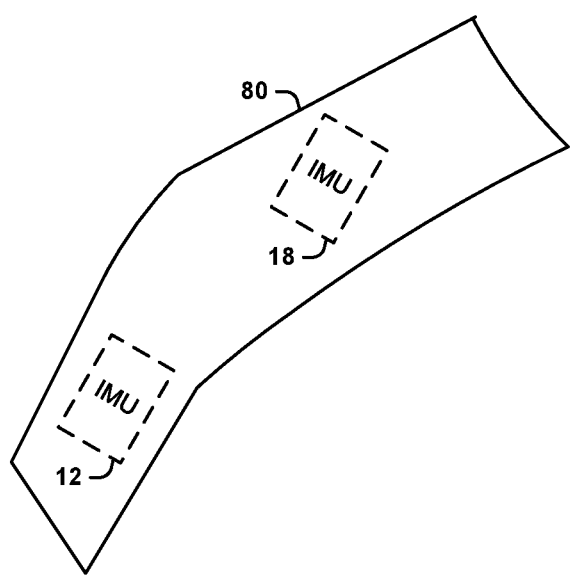
FIG. 10 is a schematic diagram of a compression garment housing the wearable device of FIG. 9.

Referring now to FIG. 9, illustrated is an example of the wearable device 11 that includes the IMU device 12 and a second IMU device 18, which can be time-correlated and calibrated together. The two IMU devices can be in wired communication or wireless communication or can communicate through the microprocessor 13. As shown in FIG. 10, one of the IMU devices 12 can be located below the kneecap, while the other IMU device 18 can be located above the kneecap. In some instances, the IMU devices 12, 18 can be located in front of and behind the kneecap to measure the inertial displacement on either side of the knee. Although not illustrated, the wearable device 11 can include the two IMU devices 12, 18 and the optical sensor 17.

IV. Methods

Figure 11:
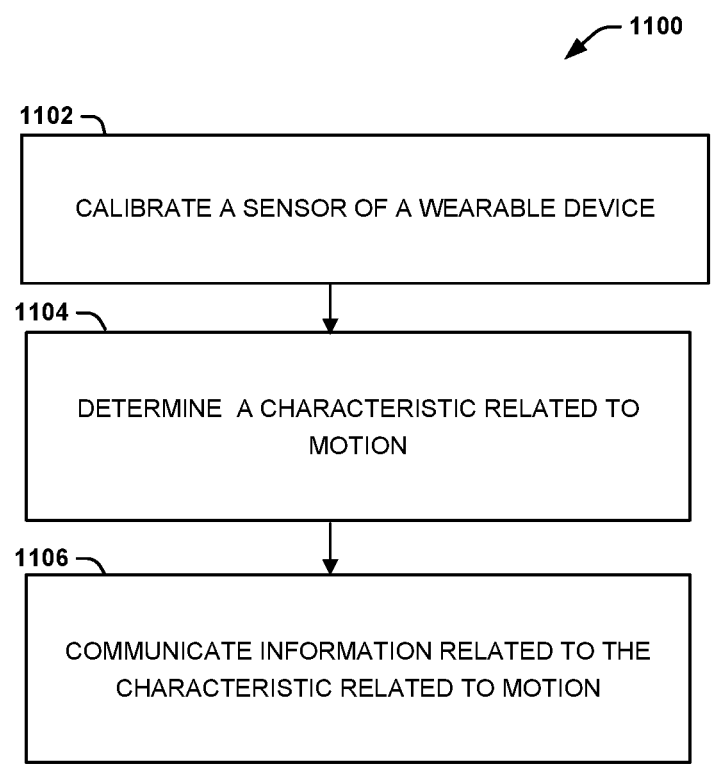
FIG. 11 is a process flow diagram of an example method for automated physical training according to another aspect of the present disclosure.

Another aspect of the present disclosure can include a method 1100 for providing automated personal training, as illustrated in FIG. 11. The method 1100 can be performed by the system 10 or 20 of FIGS. 1 and 2 using the wearable device 11 shown in FIGS. 3-10. The wearable device 11 can include at least one inertial measurement unit (IMU) device and a secondary sensor (like an optical sensor or a resistive sensor).

At 1102, an inertial measurement unit (IMU) device of a wearable device worn by an athlete around a joint can be calibrated for the first time. This calibration should be done while the athlete is standing still. Part of the calibration can include setting an anatomical reference frame. Then, at 1104, based on inputs from the IMU device (which may include information recorded by another sensor), determining a characteristic related to motion. For example, the characteristic related to motion can be based on a rotation from the anatomical reference frame, a speed, and a distance traveled. In some instances, the angle of the joint, measured with an optical sensor, a potentiometer, and/or another IMU device, can also be considered. At 1106, information related to the characteristic related to motion of the joint can be communicated to an external device. In some instances, the external device can perform additional processing tasks. For example, the external device can perform a full gait analysis based on the information provided. Additionally, the external device 9 can communicate with the wearable device worn by the athlete in a bi-directional manner.

Figure 12:
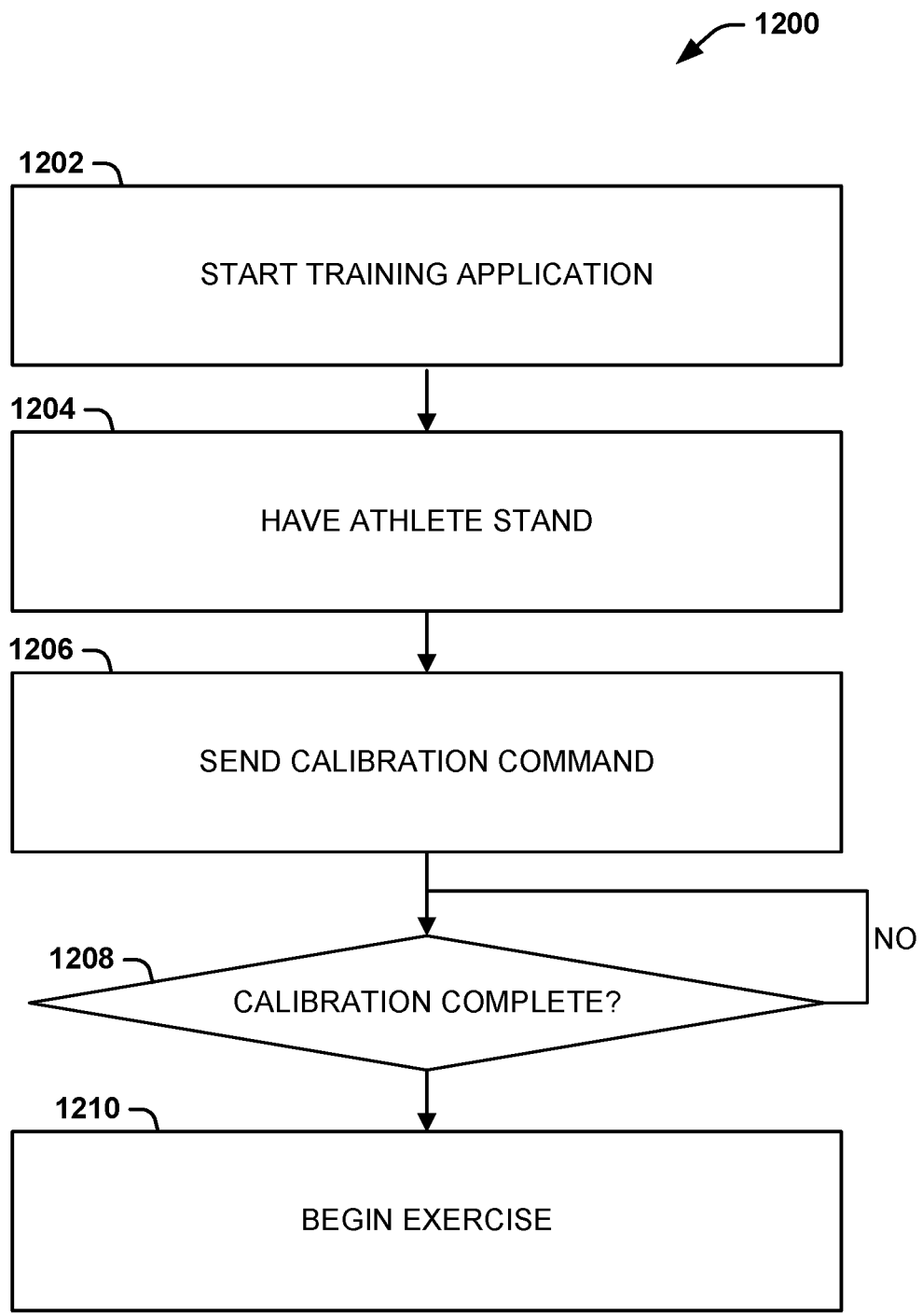
FIGS. 12-14 are process flow diagrams of example method for calibrating the wearable device used for physical training.
Figure 13:
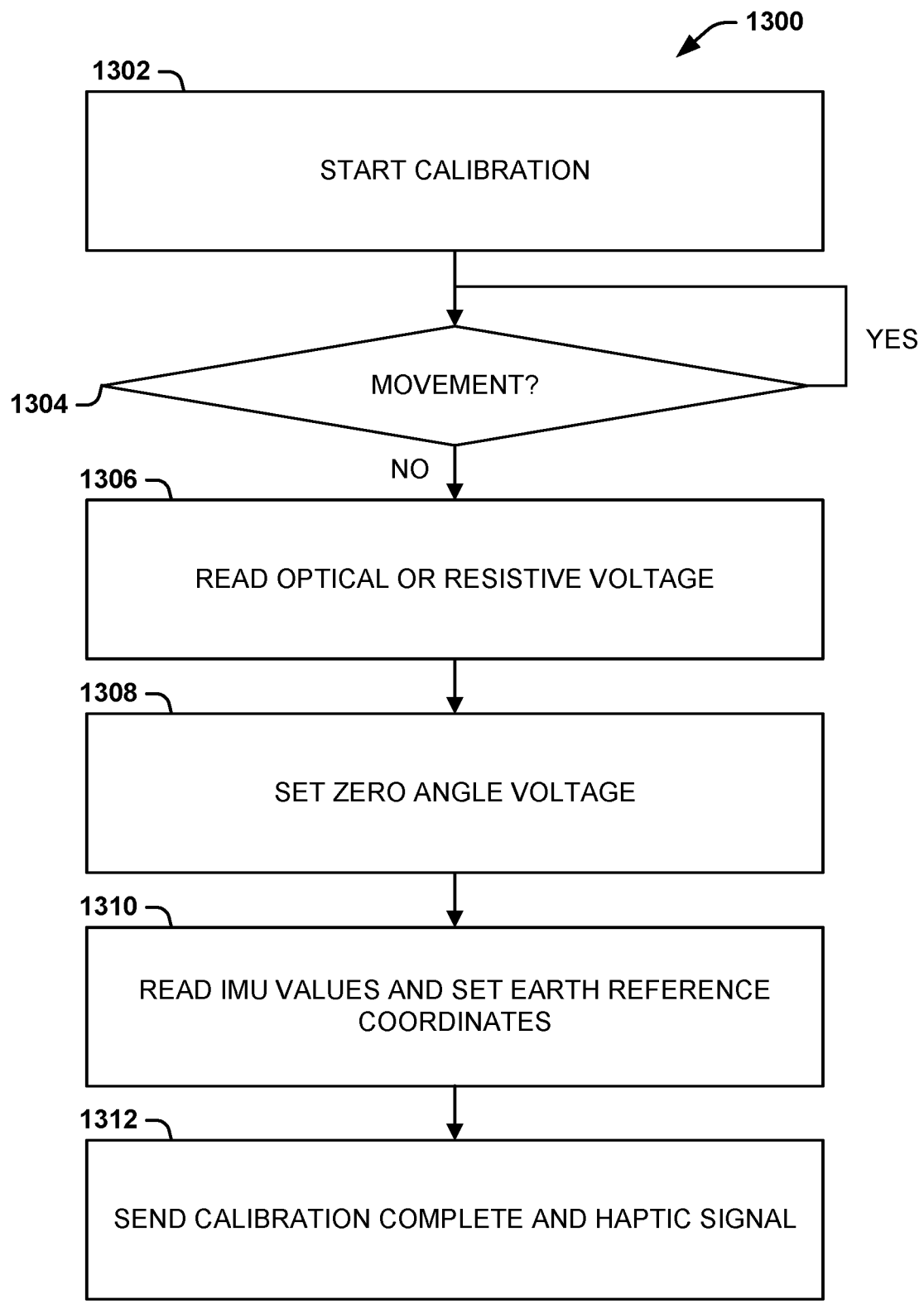
Figure 14:
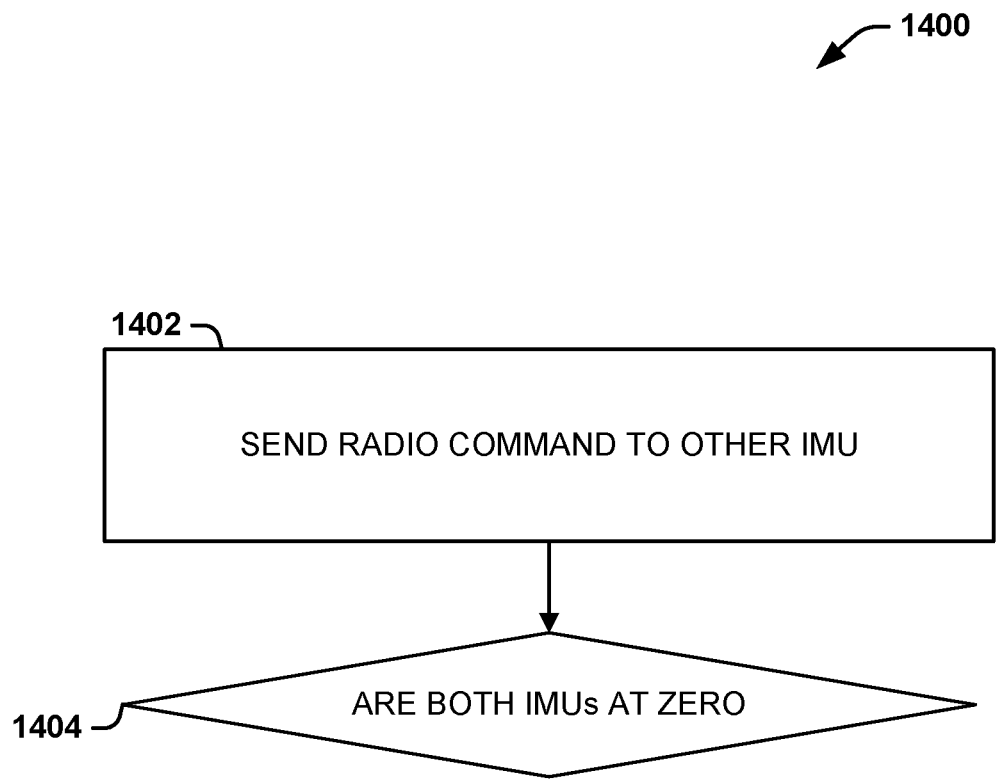

Different examples of self-calibration are shown in FIGS. 12-14. In FIG. 12, at 1202, the training application can be started. The initial calibration can commence. At 1204, the athlete can stand (standing straight corresponds to a knee angle=0) for a time (e.g., 5 seconds) and at 1206, a calibration command can be sent. At 1208, a determination can be made if the calibration is complete. If the calibration is complete, at 1210, the exercise can begin.

The self re-calibration can be accomplished according to FIG. 13. The self-recalibration can occur while the athlete is moving. At 1302, the calibration can be started. At 1304, it can be determined whether the joint is moving. When the athlete is moving, the joint will not be moving at some points of the athlete's movement. If the joint is not moving, at 1306, the optical or resistive voltage can be read (from the optical or resistive sensor). At 1308, a zero angle voltage can be set based on the optical or resistive voltage. At 1310, IMU values can be read, and the earth reference coordinates can be set. At 1312, a calibration complete and haptic signal can be sent.

FIG. 14 provides an additional step, where (after no movement is detected) at 1402, one IMU sends a radio command to another IMU stating that "I am at zero". At 1404, it is determined whether both IMUs are at zero. If both are not at zero, the method goes back to the "is there movement" step. However, if both are at zero, the method proceeds to reading the optical or resistive voltage.

From the above description, those skilled in the art will perceive improvements, changes and modifications. Such improvements, changes and modifications are within the skill of one in the art and are intended to be covered by the appended claims.

The following is claimed:

1. A wearable device comprising:
an inertial measurement unit (IMU) device configured to be located at a position below a knee of an athlete and adapted to measure an inertial displacement of the knee, wherein the inertial displacement is related to the valgus angle of the knee;
an optical sensor connected to the IMU device, configured to traverse the knee in a vertical direction and adapted to measure an angle of the knee;
a microprocessor associated with the IMU device configured to receive data related to the inertial displacement of the knee and data related to the angle of the knee during an exercise, to create a motion data set comprising the data related to the inertial displacement of the knee calibrated to be relative to an anatomical reference frame and the data related to the angle of the knee, and to compare the motion data set to at least one pre-determined scoring metric for the exercise to determine an output indication of motion that indicates a proper movement of the knee or an improper movement of the knee;
a power source; and
a tactile output device coupled to the microprocessor and configured to provide tactile feedback based on the output indication of motion indicating the proper movement of the knee or the improper movement of the knee.

2. The wearable device of claim 1, further comprising an additional IMU device configured to be located at a position opposed to the IMU device below the knee of the athlete and adapted to measure an inertial displacement of an opposite side of the knee.

3. The wearable device of claim 2, wherein the additional IMU device is time correlated with the IMU device to provide the valgus angle of the knee based on the inertial displacement recorded by the IMU device and the inertial displacement of the opposite side of the knee recorded by the additional IMU device.

4. The wearable device of claim 1, wherein the optical sensor comprises a fiber optic sensor.

5. The wearable device of claim 1, wherein the wearable device is a compression garment sized and dimensioned to be located around the knee, wherein the IMU device, the optical sensor, the processor, the power source, and the tactile output device are embodied within the compression garment.

6. The wearable device of claim 5, wherein the compression garment comprises a potentiometric structure.

7. The wearable device of claim 1, further comprising a wireless transceiver to communicate with an external device to establish the anatomical reference frame.

8. A system comprising:
an external device comprising a wireless transceiver;
a plurality of wearable devices, each comprising:
an inertial measurement unit (IMU) device configured to be located at a position below a joint of a respective athlete and adapted to measure an inertial displacement of the joint, wherein the displacement is related to a valgus angle of the joint;
an optical sensor, connected to the IMU device, configured to traverse the joint of the respective athlete in a vertical direction and configured to measure an angle of the joint;
a microprocessor associated with the IMU device configured to receive data related to the inertial displacement of the joint and data related to the angle of the joint during an exercise, to create a motion data set comprising data related to the inertial displacement of the joint and data related to the angle of the joint, and to compare the motion data set to a pre-determined scoring metric for the exercise to determine an output indication of motion that indicates a proper movement of the joint or an improper movement of the joint;
a wireless transceiver coupled to the microprocessor;
an output device coupled to the microprocessor and configured to provide tactile feedback or audio feedback based on the output indication of motion indicating the proper movement of the knee or the improper movement of the joint; and
a power source,
wherein the wireless transceiver of the external device is configured to facilitate bidirectional communication with the wireless transceiver of each of the plurality of wearable devices.

9. The system of claim 8, wherein the joint is a knee, an ankle, an elbow, spine or a shoulder.

10. The system of claim 8, wherein the external device comprises a watch, a mobile telephone, a tablet computing device, a laptop, or a desktop.

11. The system of claim 8, wherein the external device stores, in a non-transitory memory, training exercises and software for scoring the training exercises based on the motion data set.

12. The system of claim 8, wherein the external device monitors the plurality of wearable devices, wherein each of the plurality of wearable devices is associated with one of a plurality of joints.

13. The system of claim 8, wherein at least one of the external device and each microprocessor of each wearable device executes the kinetic algorithm to determine the output indication of motion.

* * * * *